United States Patent [19]

Christiansen

[11] Patent Number: 4,935,373
[45] Date of Patent: Jun. 19, 1990

[54] REFERENCE LIQUID

[75] Inventor: Torben F. Christiansen, Holte, Denmark

[73] Assignee: Radiometer A/S, Copenhagen, Denmark

[21] Appl. No.: 294,908

[22] Filed: Jan. 6, 1989

Related U.S. Application Data

[60] Continuation of Ser. No. 73,906, Jul. 13, 1987, abandoned, which is a continuation of Ser. No. 863,179, May 14, 1986, abandoned, which is a continuation of Ser. No. 725,525, Apr. 23, 1985, abandoned, which is a continuation of Ser. No. 408,605, Aug. 16, 1982, abandoned, which is a division of Ser. No. 162,430, Jun. 24, 1980, Pat. No. 4,363,633.

[30] Foreign Application Priority Data

Jun. 28, 1979 [DK] Denmark ................................ 2747

[51] Int. Cl.$^5$ ........................ G01N 27/56; C09K 3/00
[52] U.S. Cl. .................................... 436/18; 252/408.1; 436/19
[58] Field of Search .............................. 436/8, 18, 19; 252/408.1

[56] References Cited

U.S. PATENT DOCUMENTS

| | | | |
|---|---|---|---|
| 3,293,134 | 12/1966 | Lenahan et al. | 252/408.1 X |
| 3,799,883 | 3/1974 | Dennis et al. | 252/408.1 |
| 3,932,233 | 1/1976 | Ruzicka et al. | 252/62.2 X |
| 3,941,565 | 3/1976 | Schwartz | 23/230 B |
| 4,126,575 | 11/1978 | Louderback | 252/408.1 |
| 4,363,633 | 12/1982 | Christiansen | 436/19 |
| 4,529,705 | 7/1985 | Larsen | 436/18 X |

OTHER PUBLICATIONS

Moore, *Jour. Clin. Invest.*, vol. 49, 1970, pp. 319-334, "Ionized Calcium in Normal Serum ...".
Good, et al., *Biochem.*, vol. 5, 1966, pp. 467-477, "Hydrogen Ion Buffers ...".
Ladenson, et al., *Clin. Chem.*, vol. 19, 1973, pp. 565-574, "Free Calcium in Serum ...".
Seamonds, et al., *Clin. Chem.*, vol. 18, 1972, pp. 155-160, "Determination of Ionized Calcium ...".
Mohan, et al., "Standardization of Ion-Selective ...., "*Nat'l Bureau of Standards Special Publication*, 450, Jul. 1975, pp. 293-299.
Schwartz, "Serum Ionized ...", *Clin. Chim. Acta*, 64(1975) 227-239.
Kim, et al., "Determinator of Free Ca ...", *Anal. Bioch.*, 89 (1978) 521-528.
Ladenson, et al., "Use of Tris Bufus ..." *Clin. Chem.* vol. 20, No. 10, 1974.
Sandell, "Procedure for the Preparation ...", *Textbook of Quantitative Inorganic Analysis*, MacMillan Co., New York 1964 pp. 526-527.
Sankar, et al., "Buffers ...", *Anal. Chem. vol. 50, Nov. 1978 pp. 1922-1924*.

*Primary Examiner*—Mary C. Lee
*Assistant Examiner*—Catherine S. K. Scalzo
*Attorney, Agent, or Firm*—Bryan, Cave, McPheeters & McRoberts

[57] ABSTRACT

A reference liquid for calibration or quality control of instruments which determine ionized calcium and pH. The reference liquid contains both a particular calcium ion activity and a pH-buffer and can therefore be used for calibration of both the calcium-sensitive electrode and the pH-electrode in the instruments. The pH-buffer is a nitrogen-containing organic sulphonic acid and the salt of this acid, the acid having a pK in the range of 6.6-7.6. The reference liquid has an ionic strength of 0.15-0.17, a buffer capacity $\beta$ in the range of 0.04-0.10 and is packed in glass ampoules.

6 Claims, No Drawings

REFERENCE LIQUID

This is a continuation, of U.S. application Ser. No. 073,906, filed July 13, 1987, which is a continuation of U.S. application Ser. No. 863,179, filed May 14, 1986, which is a continuation of U.S. application Ser. No. 725,525, filed Apr. 23, 1985, which is a continuation of U.S. application Ser. No. 408,605, filed Aug. 16, 1982, all now abandoned, which is a divisional of U.S. application Ser. No. 162,430, filed June 24, 1980 now U.S. Pat. No. 4,363,633.

The present invention relates to a reference liquid for calibration or quality control of instruments which are adapted to determine the content of ionized calcium in liquid samples.

It is known that the activity or concentration of calcium ions in biological liquids is critical to many important biological processes. The content of ionized calcium in serum or plasma is of a special interest as it plays an important role in the total calcium metabolism. In recent years, calcium-sensitive electrodes have been provided which permit an exact and relatively simple determination of ionized calcium. An example of these electrodes is described in U.S. Pat. No. 3,932,233. This electrode comprises an internal reference system and a membrane adapted to be contacted with the liquid the calcium ion activity of which is to be determined. The membrane contains a calcium ion exchanger, e.g. calciumdi-(p-n-octylphenyl)-phosphate which, during use of the electrode, is in electrical contact with the internal reference which may, e.g., be a silver/silver chloride electrode. The other known electrodes for determining calcium ion activities are also based on the use of calcium ion exchangers.

It is known that the content of ionized calcium in serum is pH-dependent, which is especially due to the fact that the binding of calcium to serum proteins is pH-dependent. For this reason it is important to determine the pH of a serum sample together with its calcium ion activity, either in order to report the measured set of calcium ion activity and pH or to perform a conversion of the calcium ion activity into the calcium ion activity which would be present in the sample at a predetermined "normal" pH, for example 7.40. The relation between ionized calcium and pH is discussed, e.g., by Moore in "The Journal of Clinical Investigation", volume 19, 1969, pages 318–334, and in U.S. Pat. No. 3,941,565. Therefore, the most suitable instruments for determining ionized calcium in biological liquids are instruments in which the liquid sample in which the content of ionized calcium is to be determined is measured both with a calcium-sensitive electrode and with a pH-electrode.

Like in other electrochemical measuring electrodes, the calcium and the pH-electrodes in such instruments for determining the calcium ion activity must, with regular intervals, be calibrated with reference liquids showing known exact values for the quantity which is to be determined with the electrode in question. In the practical use of such instruments, this calibration is preferably performed with commercial reference liquids which have been prepared and packed in such a manner that they are long term-stable with retention of their manufacturer-declared data, and which are packed in suitable unit dosis packages from which they are easily transferred to the instrument to be calibrated. For the calibration of pH-electrodes, it has been known for several years to use phosphate-buffered solutions packed in glass ampoules. However, phosphate buffers are not desirable for use in instruments containing calcium-sensitive electrodes as a contamination of a calcium-sensitive electrode with phosphate would disturb the function of the electrode. For the calibration of calcium-sensitive electrodes it is known to use, e.g., commercial reference solutions containing 150 millimoles NaCl/liter and 1.00 and 2.00, respectively, millimoles $CaCl_2$/liter.

As a calibration of an electrode usually involves measuring the electrode against two different reference liquids, each showing its particular level of the quantity to be measured, the calibration of the above-mentioned instruments for determining calcium ion activity and pH involves the use of four different reference liquids, two for calcium and two for pH. It would be a great advantage in the operation of such instruments to be able to calibrate the calcium-sensitive electrode and the pH-electrode simultaneously on the reference solution so that the calibration of the two electrodes of the instrument could be performed on one and the same type of reference liquid with two different levels for calcium activity and pH. However, such a combined reference liquid for simultaneous calibration of calcium electrodes and pH-electrodes must fulfil several requirements which would partly seem mutually incompatible.

To be useful for the calibration of the pH-electrode, the calcium ion-containing reference liquid must contain a pH-buffer system, but this pH-buffer system must not interfere with the calcium measurement. Hence, the constituents of the pH-buffer system must not be soluble in the calcium membrane of the calcium-sensitive electrodes, it must not precipitate calcium ions, and its binding of calcium ions must be stable under the conditions of storage and use which prevail in practice. Furthermore, it is important that the liquid junction potential between the pH-buffer system and a strong KCl-solution used as electrolyte in the reference electrode system is reproducible and preferably the same as in serum. The pH-buffers which are known for use in commercial long term-stable reference liquids do not fulfil these requirements. Furthermore, the pH-buffer should be stable under autoclaving (heating to 121° C.).

When the reference liquid is to be used for determining pH in physiological liquids such as serum/plasma, its pH at 37° C. should optimally be at about 7.4 which is the normal pH in serum/plasma, and at about 6.8, and the pH-buffer system must be selected in view of this.

(As a pH different from 7.4, a high pH could be selected, for example a pH of 8, but this would not be in conformity with the existing pH-standards for measuring pH in serum/plasma, and furthermore, such a reference liquid would have a too high affinity to $CO_2$, which would result in the formation of carbonate ions, with which calcium ions may be precipitated as calcium carbonate, which, of course, is undesirable in a reference liquid for determining calcium.)

Finally, the pH-buffer in the reference liquid should have a sufficiently high buffer capacity.

According to the present invention it has been found that a particular type of pH-buffers, that is, buffers consisting of a nitrogen-containing organic sulphonic acid and the salt of this acid, the acid having a pH-value in the range of 6.6–7.6 at 37° C., excellently fulfils all of the above-mentioned conditions, and that calcium ion-containing reference liquids containing these buffers show a number of surprisingly advantageous properties.

It has been found that (a) buffers of the above-mentioned kind do not interfere with the indication of the calcium electrode, (b) calcium is bound to the buffers to a low degree ($CaA/A \times Ca^{++} = 2-3$), (c) ionized calcium in the reference liquid may be measured with high exactitude versus a suitable calcium ion standard, (d) the pH in the reference liquid may be measured with high exactitude versus a suitable pH standard, (e) the reference liquid containing buffers of the above-mentioned kind may be autoclaved without change of the calcium ion activity and the pH, (f) the reference liquid is long term-stable, both with respect to the calcium ion activity and with respect to the pH, and (g) it has proved possible to store the reference liquid in, for example, 3 ml glass ampoules without any significant change of the calcium ion activity or the pH during long term storage, which in itself is surprising as ampoule glass contains calcium and as one would have feared that ampoule calcium (and ampoule zinc which would be capable of interfering with the calcium measurement) would be liberated into the liquid in the ampoule.

Hence, the invention relates to a reference liquid for simultaneous calibration or quality control of the calcium-sensitive electrode and the pH-electrode in instruments adapted for determining the content of ionized calcium in liquid samples, the said reference liquid containing, at a particular temperature, a particular calcium ion activity, and the said reference liquid containing a pH-buffer which consists of a nitrogen-containing organic sulphonic acid and the salt of the acid, the acid having a pK in the range of 6.6–7.6 at 37° C.

pH-Buffer systems consisting of a nitrogen-containing organic sulphonic acid and the salt of the acid constitute a known class of buffer systems described, for example, in Biochem., 5, (1966), 467, and Analytical Chemistry, 50, (1978) 1922. Examples of such acids, which may also more particularly be characterized as alkane sulphonic acids with nitrogen-containing basic groups attached to the alkane moiety, the alkane moiety especially being ethane or propane (in other words, the alkane moiety contains, in particular, 2-2 carbon atoms), via a nitrogen atom in the nitrogen-containing basic groups, are 3-(N-morpholino)propane sulphonic acid (MOPS), pK 7.18 at 25° C., piperazine-N,N'-bis(2-ethane sulphonic acid) (PIPES), pK 6.8 at 20° C., N-(2-acetamido)-2-aminoethane sulphonic acid (ACES), pK 6.9 at 20° C., N,N-bis(2-hydroxyethyl)-2-aminoethane sulphonic acid (BES), pK 7.15 at 20° C., N-tris(hydroxymethyl)methyl-2-aminoethane sulphonic acid (TES), pK 7.5 at 20° C., and N-2-hydroxyethylpiperazine-N-2-ethane sulphonic acid (HEPES), pK 7.55 at 20° C.

The reference liquid of the invention is normally composed for optimal use at the temperature which is the normal working temperature of the instruments for determining calcium ion activity which are to be calibrated or subjected to quality control using the reference liquid, i.e., the temperature to which the instrument thermostates the samples introduced in the instrument, e.g., 37° C. or 25° C., and the ionic strength of the reference liquid preferably corresponds to the ionic strength of an isotonic salt solution, i.e. 0.15–0.17. At 37° C. and an ionic strength of 0.15, the above-mentioned pK values decrease with 0.25–0.35. As example may be mentioned that BES, which at 37° C. and an ionic strength of 0.15 has a pK of 6.9, is suitable for preparing a pH-buffer with pH 6.8 (HBES:BES = 1.25:1), TES, which at 37° C. and an ionic strength of 0.15 has a pK of 7.22, is suitable for preparing a pH-buffer with pH 7.4 (HTES:TES = 1:1.5), and HEPES, which at 37° C. and an ionic strength of 0.15 has a pK of 7.34, is suitable for preparing a pH-buffer with pH 7.4 (HHEPES:HEPES = 1:1.15).

A suitable buffer anion concentration in the reference liquid of the invention is 0.03–0.07 mol/liter, preferably about 0.05 mol/liter, and it is preferred that the corresponding cation is an alkali metal cation, and it is especially preferred that it is the sodium ion. A perhaps more suitable indication of the concentrations of buffer which should be used in the reference liquid of the invention is an indication of the buffer capacity to be aimed at in the system. According to the invention, this buffer capacity is in the range between 0.04 and 0.10, especially in the range of 0.05–0.08. Thus, the buffer capacity $\beta$ for TES/HTES in an anion concentration of 0.05 mol/liter, corresponding to a total buffer concentration of 0.125 mol/liter, is 0.0695, for BES/HBES with a buffer anion concentration of 0.05 mol/liter, corresponding to a total buffer concentration of 0.1125 mol/liter, it is 0.0695, and for HEPES/HHEPES in a buffer anion concentration of 0.05 mol/liter, corresponding to a total buffer concentration of 0.1075 mol/liter, it is 0.0617.

The buffer capacity $\beta$ is in this connection calculated from the formula $$\beta = 2.303 \times c \times (K_a \times 10^{-pH}) / (K_a + 10^{-pH})^2,$$

where c = the total concentration of the buffer system, and $K_a$ = the acid dissociation constant of the buffer system.

With respect to its calcium content, the reference liquid of the invention may suitably be a predominant solution of free calcium ions, for example provided by adding a soluble calcium salt such as $CaCl_2$. Another possibility is to use a calcium buffer. If a calcium buffer is used, the properties of the ligand must be well-documented and fulfil the same conditions as mentioned above for the pH-buffers. The conditional binding constant for calcium ions must be in the range $10^2$–$10^4$ $mol^{-1} \times liter$ at pH 7, and, e.g., nitrilotriacetic acid (NTA) and citrate fulfil these conditions.

A suitable set of reference liquids according to the invention is, for example, a set which consist of a reference liquid being 2.5 millimolar with respect to calcium ions and having a pH of about 6.8, and a reference liquid being about 1.25 millimolar with respect to calcium ions and having a pH of about 7.4. The ionic strength of the two reference liquids in a set should be the same and is suitably either 0.150 at 25° C. or 0.160 at 25° C. In the literature (e.g., J. H. Ladenson and G. N. Bowen, Clin. Chem., 19, (1973), 565, and B. Seamonds et al., Clin. Chem., 18, (1972), 155), the ionic strength for the standards used in connection with the measurement of ionized calcium has been about 0.150, but to-day, there is a trend that standards for electrochemical measurement of electrolytes in serum should be based on an ionic strength of 0.160 (cfr., e.g., M. S. Mohan and R. G. Bates, NBS Special Publication July 1975, page 293, and H. D. Schwartz, Clin. Chem. Acta, 64, (1975), 227). Siggaard-Andersen (The Acid-Base Status of the Blood, Munksgaard, Copenhagen 1974, page 37) states the ionic strength in serum to be 0.17. The desired ionic strength in the reference liquid according to the invention is suitably provided by the addition of NaCl.

The primary standards against which the reference liquid of the invention is measured in the production stage are standards for calcium and pH, respectively, which are selected with a view of obtaining the greatest possible exactitude and reproducibility. Suitable primary calcium standards may be based upon calcium carbonate as a reference material, as calcium carbonate may be obtained as a very pure substance and conventionally is a primary reference material for determinations of total calcium in serum, and the primary calcium standards are prepared herefrom by weighing or methods directly derived therefrom, vide the experimental section. Suitable primary standards are, e.g., a standard which is 1.25 millimolar with respect to $CaCl_2$ and 146.25 millimolar with respect to NaCl, the said standard having, at 25° C., an ionic strength of 0.150, and a standard which is 2.50 millimolar with respect to $CaCl_2$ and 142.50 millimolar with respect to NaCl, the said standard having, at 25° C., an ionic strength of 0.150. (At 37° C. the molar concentration and the ionic strength will be 0.4% lower.)

The calcium activity in standards based on an ionic strength of 0.150 will be 1.2–1.5% higher than a standard based on an ionic strength of 0.160, under the presumption that the standards are measured against each other with a saturated calomel reference electrode. However, the discrepancy between the standards having different ionic strengths only manifests itself because ionized calcium in serum is conventionally stated in concentration units instead of using an activity scale, where the result will be independent of the ionic strength of the standard used.

When using the above-mentioned standards with an ionic strength of 0.150, there is established a new activity scale which is proportional with the true activity with a proportionality factor of about 3.4.

The primary standards for use in the production stage for measuring the pH of the reference liquid are suitably conventional phosphate precision buffers having a pH of 6.8 and 7.4, respectively, for example, "S1500" (composition 3.402 grams of $KH_2PO_4$, 4.450 grams of $Na_2HPO_4.2H_2O$, 1,000 kg of water, pH 6.881 at 20° C.) and "S1510" (composition 1.816 grams of $KH_2PO_4$, 9.501 grams of $Na_2HPO_4.2H_2O$, 1.000 kg of water, pH 7.426 at 20° C.) from Radiometer A/S, Copenhagen.

In using the reference liquid of the invention for the calibration of instruments for measuring ionized calcium, one suitably proceeds as follows: Two correlated reference liquids are introduced consecutively in the sample introduction system of the instrument and the read-out or the indication of the calcium electrode and the pH-electrode, respectively, is adjusted to the values which are stated on the respective reference liquids. The introduction of the reference liquid in the measuring instrument may be performed in any conventional manner, but it is particularly preferred that both the sample and the reference liquid are introduced in the measuring instrument by means of a dispenser of the type described in Danish patent application Ser. No. 3966/78 and in U.S. patent application Ser. No. 11,947 of Feb. 13, 1979. For use in such a dispenser, the reference liquid is suitably packed in ampoules, preferably 3 ml ampoules, suitably made of Fiolax-glass. Apart from the fact that glass ampoules make it possible to utilize the above-mentioned dispenser, glass ampoules are generally a particularly suitable and desirable packing form for reference liquids and as mentioned above, it has surprisingly been found that even on storage in glass ampoules for a long time, the reference liquid of the invention shows a very high degree of exactitude with respect to its values for calcium and pH.

Analytical Biochemistry 89, 521–528 (1978) describes the use of a calcium-containing solution being 0.1 molar with respect to KCl and 20 millimolar with respect to HEPES in connection with the calibration of a calcium-sensitive electrode. In that connection, however, HEPES in only used to stabilize the pH in the calcium measurement, and there is no disclosure or indication of the fact that the liquid in question might be useful for simultaneous calibration of the calcium electrode and a pH-electrode, nor does the liquid in question have a buffer constant $\beta$ being in the desired range for this purpose, as the buffer constant $\beta$ of the liquid in question, calculated according to the above-stated equation, is 0.0115, nor does the liquid have an ionic strength in the practical range of 0.15–0.17, but has, on the contrary, a much lower ionic strength (0.12).

M. S. Mohan and R. G. Bates, NBS Special Publication July 1975, 293, describe the use of a standard which is a mixed standard for Na, K, Ca, Cl and pH, in which the pH-system used is TRIS HCl/TRIS. Such a buffer system would not be suitable for the purpose of the present invention. Firstly, the buffer system has a pK-value of 7.85 at 37° C. which means that the buffer had to be very unsymmetrically composed in order to obtain a pH about 7.4 (TRIS HCl: TRIS=3:1), which would result in the buffer capacity becoming low compared with the total concentration of the buffer, as it must be born in mind that the requirement to an ionic strength in the above-mentioned range sets a limit of about 0.15M TRIS HCl. It would be disadvantageous to let TRIS HCl/TRIS dominate the solution as this would result in a great liquid junction/potential difference (of the order of 2.5 mvolt) compared to the primary phosphate pH-standards (R. A. Durst and R. G. Bates, NBS Special Publication July 1975, 293). Furthermore, discrepancies have been observed between the TRIS-buffer and the phosphate buffer when these are measured versus each other on different pH-blood gas equipment (J. H. Ladenson et al., Clin. Chem., 20, (1974), 1337). Finally, it would not be possible to use a TRIS-buffer with pH 6.8 as pH-standard due to the still lower buffer capacity at this pH (TRIS HCl: TRIS=10:1).

The reference liquid according to the present invention and its remarkable properties and surprising stability properties which are further documented in the experimental section are, thus, not obvious on the background of the above-mentioned literature references.

EXPERIMENTAL SECTION

The invention is further elucidated in the following examples, where the following materials and procedures are used:

| | |
|---|---|
| Calcium carbonate: | Calciumcarbonat zur Analyse, Urtitersubstanz, Merck No. 2060. |
| Sodium chloride: | Natriumchlorid, Suprapur, Merck No. 6406, calcium content: max. $1 \times 10^{-5}$%. |
| Hydrochloric acid: | Salzsaure min. 30% Suprapur, Merck No. 318, calcium content: max. $5 \times 10^{-6}$%. |
| TRIS: | Tris(hydroxymethyl)amino methane, TRIZMA BASE, Sigma No. T1503 Reagent |

|  |  |
|---|---|
|  | Grade, Crystalline, Approx. 99.9%. |
| Deionized water: | carbon dioxide-free, conductivity: <1 μS. |
| TES: | Sigma No. T1375, anhydrous, molecular weight 229.2. |
| BES: | Sigma No. B9879, anhydrous, molecular weight 213.3. |
| 1M Sodium hydroxide solution: | Is prepared as described by I. M. K. Kolthoff and E. B. Sandell in "Textbook of Quantitative Inorganic Analyses", The Macmillan Company, New York, 1964, page 526 ff. |

In preparing calcium standards and reference liquids the equipment used must be equipment which does not release calcium or any other compound which would influence a calcium ion determination to the liquid prepared. Suitably, especially cleaned glass equipment of Duran or Pyrex which does not contain calcium in the glass can be used. The equipment is first cleaned with 10% hydrocloric acid for 24 hours and is thereafter thoroughly washed with deionized water. As parent solution, for use in the primary calcium standard, a 0.1M calcium chloride solution is prepared by dissolving calcium carbonate in deionized, carbon dioxide-free water and an excess of 30% pure hydrocloric acid and boiling off the carbon dioxide.

The primary standards used, designated "1.25 mM Ca" and "2.50 mM Ca", respectively, are prepared as follows:

(a) "1.25 mM Ca":

12.50 ml 0.1000M calcium chloride solution, 8.488 grams of sodium chloride, 0.1211 grams of TRIS and about 950 ml of deionized water are agitated until all solid substance has dissolved, the pH is adjusted to 7.38 with hydrochloric acid, and the solution is filled up with deionized water to a total volume of 1 liter. The solution is poured in clear Fiolax-glass ampoules which are sealed and autoclaved.

The final solution has the following composition:
1.250 mM $Ca^{++}$
145.25 mM NaCl
1.00 mM Tris
pH=7.40
I=0.150M.

(b) "2.50 mM Ca":

25.00 ml 0.1000M calcium chloride solution, 8.269 grams of sodium chloride, 0.1211 grams of TRIS and about 950 ml of deionized water are mixed and agitated until all solid substance has dissolved, the pH is adjusted to 6.84 with hydrochloric acid, and deionized water is added to a total volume of 1 liter. The solution is poured in clear Fiolax-glass ampoules which are sealed and autoclaved.

The final solution has the following composition:
2.500 mM $Ca^{++}$
141.5 mM NaCl
1.00 mM Tris
pH=6.85
I=0.150M.

EXAMPLE 1

To 19.07 grams of TES, 14.30 ml 0.1000M calcium chloride solution, 50.286 ml 1M sodium hydroxide solution and 5.597 grams of sodium chloride is added deionized, carbon dioxide-free and germ-free water to a total volume of 1000 ml, and the components are agitated under argon until all solid substance has dissolved. The final reference liquid is maintained under argon and is control-measured as to pH-value and ionized calcium as explained below.

When the reference liquid has been control-measured and possibly adjusted, it is poured into 3 ml ampoules of clear Fiolax-glass under an argon atmosphere, the ampoules first being flushed with argon. The ampoules are sealed and heated to 120° C. for 20 minutes, the heating from 100° to 120° C. and the cooling from 120° to 100° C. being performed in the course of 10 minutes.

The reference liquid prepared has a free calcium ion concentration of 1.25 mM, a pH of 7.383 and an ionic strength of 0.150.

EXAMPLE 2

In the same manner as described in Example 1, a reference liquid is prepared from 22.98 grams of BES, 27.51 ml 0.1000M calcium chloride solution, 50.578 ml 1M sodium hydroxide solution, 5.357 grams of sodium chloride and deionized, carbon dioxide-free and germ-free water to a total volume of 1000 ml, the reference liquid being poured into 3 ml ampoules of glass in the same manner as described in Example 1.

The reference liquid prepared has a free calcium ion concentration of 2.50 mM, a pH of 6.841 and an ionic strength of 0.150

The reference liquids prepared in Examples 1 and 2 are control-measured as to pH and ionized calcium at 37° C. The measurements are carried out as comparative, relative potentiometric measurements. The pH-electrode is calibrated on phosphate buffers with known corrections. The calcium electrode is calibrated on "1.25 mM Ca" and "2.50 mM Ca" standard solutions.

If the control-measurement shows that the reference liquid deviates from the above-mentioned values, an adjustment of the reference liquid is performed in the following manner:

If the content of calcium ions is found to be higher than the declared value, the calculated amount of deionized, carbon dioxide-free and germ-free water is added. If the calcium ion content is too low, the calculated amount of 0.1000M calcium chloride solution is added. Any deviation of the pH-value from the desired value is adjusted by adding either the calculated amount of sodium hydroxide solution or the calculated amount of hydrochloric acid. After this possible adjustment of the main batch, control-measurement is performed to secure that the future reference liquid now shows the declared values.

EXAMPLE 3

Two reference liquids are prepared and long term-tested to determine their long term-stability. The reference liquids are prepared as follows:

"TES 1.25"

Is prepared in similar manner as described in Example 1 from 27.958 grams of NaCl, 96.24 grams of TES, 71.50 ml 0.1000M calcium chloride solution and 253.33 ml 0.9928 molar sodium hydroxide solution and deionized, carbon dioxide-free and germ-free water to a total volume of 5 liters.

"BES 2.50"

Is prepared in a similar manner as described in Example 1 from 26.785 grams of NaCl, 114.79 grams of BES, 137.55 ml 0.1000M $CaCl_2$ and 254.72 ml 0.9928 molar sodium hydroxide solution and deionized, carbon dioxide-free and germ-free water to a total volume of 5 liters.

After control-measurement as described above, the two reference liquids are packed in 3 ml ampoules and autoclaved in the same manner as described in Example 1. The ampoules with the reference liquid are kept at 25° C., and the data of the reference liquids is determined (measuring temperature 37° C.) over a prolonged period. The results appear from the below table, where the values stated are mean values and the standard deviations are based on 12 samples.

TABLE

| Time after preparation | TES 1.25 | | BES 2.50 | |
|---|---|---|---|---|
| | pH | mM $Ca^{++}$ | pH | mM $Ca^{++}$ |
| 1 week | 7.386 | 1.245 | 6.841 | 2.494 |
| | ±0.002 | ±0.008 | ±0.001 | ±0.009 |
| 3 weeks | 7.386 | 1.251 | 6.840 | 2.495 |
| | ±0.001 | ±0.006 | ±0.001 | ±0.011 |
| 3 months | 7.386 | 1.246 | 6.841 | 2.504 |
| | ±0.001 | ±0.006 | ±0.001 | ±0.008 |

I claim:

1. A reference liquid for the calibration or quality control of both a calcium-sensitive electrode and a pH-electrode in an instrument for determining the content of ionized calcium in a physiological liquid, said reference liquid consisting essentially of water, a calcium-containing material that simulates at a particular temperature the physiological liquid's calcium ion activity, a pH-buffer consisting essentially of a nitrogen-containing organic sulphonic acid and the salt thereof, the acid having a pK in the range of 6.6–7.6 at 37° C., the buffer capacity $\beta$ of the pH-buffer in the reference liquid being of from about 0.04 to about 0.10, and a salt in an amount providing the reference liquid with an ionic strength of from about 0.15–0.17.

2. The reference liquid of claim 1 wherein the nitrogen-containing organic sulphonic acid is an alkanesulphonic acid with a nitrogen-containing basic group attached to the alkane moiety by a nitrogen atom.

3. The reference liquid of claim 2 wherein the alkane moiety in the alkanesulphonic acid contains 2–3 carbon atoms.

4. The reference liquid of claim 3 wherein the alkane sulphonic acid is selected from the group consisting of 3-(N-morpholino)propane sulphonic acid,
piperazine-N,N'-bis(2-ethane sulphonic acid),
N-2(-acetamido)-2-aminoethane sulphonic acid,
N,N-bis(2-hydroxyethyl)-2-aminoethane sulphonic acid,
N-tris(hydroxymethyl)methyl-2-aminoethane sulphonic acid, and
N-2-hydroxyethylpiperazine-N-2-ethane sulphonic acid.

5. The reference liquid of claim 1 wherein the buffer capacity $\beta$ of the pH-buffer in the reference liquid is from about 0.05 to about 0.08.

6. The reference liquid of claim 1 wherein said reference liquid is packed in glass ampoules.

* * * * *